United States Patent [19]

Familletti et al.

[11] 4,241,174

[45] Dec. 23, 1980

[54] INTERFERON ASSAY

[75] Inventors: Philip C. Familletti, Millington; Sidney Pestka, North Caldwell; Sara Rubinstein, Passaic, all of N.J.

[73] Assignee: Hoffmann-La Roche Inc., Nutley, N.J.

[21] Appl. No.: 963,256

[22] Filed: Nov. 24, 1978

[51] Int. Cl.$^3$ ............................ C12Q 1/70; C12N 5/02
[52] U.S. Cl. ............................................. 435/5; 424/2; 424/85; 23/230 B; 435/241; 435/811
[58] Field of Search .................. 435/4, 5, 6, 811, 235, 435/241, 240; 424/2, 85; 23/230 B

[56] References Cited

U.S. PATENT DOCUMENTS 3,910,824   10/1975   Cartwright et al. ..................... 435/5

OTHER PUBLICATIONS

Armstrong, "Semi-Micro Dye-Binding Assay for Rabbit Interferon", *Applied Microbiology,* vol. 21, No. 4, (1971), pp. 723–725.

Lindenmann, et al., "Studies on Vaccinia Virus Plaque Formation and Its Inhibition by Interferon", *Virology,* vol. 19, (1963), pp. 302–309.

Green, et al., "Vesicular Stomatitis Virus Plaque Production in Monolayer Cultures with Liquid Overlay Medium: Description and Adaptation to a One-Day, Human Interferon-Plaque Reduction Assay", *J. Clin. Micro.,* vol. 4, No. 6, (1976), pp. 479–485.

Borden, et al., "A Quantitative Semi-Micro, Semi-Automated Colorimetric Assay for Interferon", *J. Lab. Clin. Med.,* vol. 89, No. 5, (1977), pp. 1036–1042.

Suzuki, et al, "Rapid and Simple Method for Assaying Interferon", *Chem. Abstracts,* vol. 83, No. 9, p. 494, (1975), Abs. No. 76834j.

*Primary Examiner*—Thomas G. Wiseman
*Attorney, Agent, or Firm*—Jon S. Saxe; Bernard S. Leon; James H. Callwood

[57] ABSTRACT

A rapid cytopathic effect inhibition assay for interferon is disclosed. The assay can be completed in about 16 hours or less, allowing its use to assist in clinical diagnosis of viral infections and also, in monitoring the production and purification of interferon whether leukocyte or fibroblast.

6 Claims, No Drawings

INTERFERON ASSAY

BACKGROUND OF THE INVENTION

Interferon is potentially a very valuable therapeutic agent in the treatment of neoplastic or viral disease states. The development of this substance into a widely available drug has been hampered by the difficulty of producing and isolating this active compound in reasonable amounts. An important aid in developing procedures for the large scale production, purification and ultimate characterization of human interferon would be the availability of an assay which could be completed in less than 24 hours.

Similarly, the presently available interferon assays are far too slow to allow practical clinical applications. It is known that blood levels of interferon are elevated above normal levels in the presence of a viral infection. Assaying of a subject's interferon levels allows the physician to determine whether a viral agent is the causative agent and allows the physician to make a rational choice in the selection of appropriate therapy. Information gained from such an assay could provide the basis for avoiding unnecessary, expensive and potentially harmful antibiotic therapy on a patient who is suffering from a viral disease which would normally be unresponsive to such therapy. Again, a critical aspect of such an assay would be the rapidity with which useful information could be made available to the physician from the time the sample is drawn. A period of three days would obviously be much too long, since it is unlikely that therapy could or should be withheld from a patient for such extended period.

A number of procedures have been known in the art to assay for interferon levels. Such assays are based on the inhibition of virus growth and measurable aspects thereof such as, for example, the virus yield, plaque number, cytopathic effect or viral products. There is presently no standard assay procedure. In general, the titers (50% end points) derived from the various assay methods are related to an internationally accepted reference preparation. The currently utilized reference is a human leukocyte interferon having a concentration of 5,000 units/ml which is held by the Medical Research Council, London, England and by the National Institutes of Health, Bethesda, Maryland.

Examples of some specific disclosed assays for interferon include a publication by Lindenmann and Gifford, Virology 19, 302 (1963) which discloses a plaque inhibition assay and a paper by John A. Armstrong, Applied Microbiology 21, No. 4, 723 (1971) which described a semi-micro dye binding assay for rabbit interferon employing quantitation of inhibition of cytopathic effects. In the Lindenmann and Gifford assay, both interferon and challenge virus were added simultaneously to chick embryo cell monolayers in bottles with an agar overlay and without the need of an absorption period of either interferon or virus. Since interferon diffuses faster than virus, and since virus was adsorbed to less than 1% of the initial target cells, all cells having been exposed to interferon under circumstances of the assay, the cells were effectively treated with interferon prior to virus exposure. After 44 to 48 hours of incubation at 37° C., the monolayers were stained with crystal violet and the plaques counted.

In the Armstrong procedure, confluent monolayer cultures of weanling rabbit kidney cells were exposed to interferon dilutions, challenged with virus, and the culture cells were stained with methylrosaniline chloride. The bound dye was then eluted and measured colorimetrically. It should be noted that the test samples, cell culture and interferon standards were incubated overnight, and after removal of the incubation medium which contained interferon, the cultured cells were treated with the challenge virus (vesicular stomatitis virus) and then incubated an additional 24 hours, or even longer, until the virus controls showed 50-90% cytopathic effects microscopically. Additional steps were required to introduce and fix the dye and to dry the preparation. It is evident that it is not possible to read the results of the assay before the third day after the procedure is started and possibly even later.

In each of the foregoing assay procedures, the test sample was added to monolayers. It has heretofore been generally believed, in the prior art, that confluent monolayers were of critical necessity to provide cells of sufficient uniformity to avoid variations in results which might be attributable to variations in cell density and/or quality of cells. It was also felt that variations in incubation times would change the susceptibility of the cells to interferon or the challenge virus in ways that would adversely affect the reproducibility and uniformity of assay results (*Interferon and its Clinical Potential*, D. A. J. Tyrell, William Heinemen Medical Books Ltd., London, 1976). In accordance with the present invention, it has unexpectedly been found that the total time for the bioassay procedure can be substantially reduced by introducing the cell culture in the form of a suspension, as opposed to the confluent monolayers thought to be essential in the prior art. In this manner, it has been found possible to add the challenge virus and the cells to the serially diluted interferon sample without the need of any prior incubation of the interferon samples and the cells.

SUMMARY OF THE INVENTION

An improved assay for interferon comprising the following steps in combination:

a. contacting a serially diluted and segregated interferon containing sample in the presence of a cell support medium with a viable cell preparation in the form of a cell suspension, said cell line known to be sensitive to the interferon type to be assayed;

b. allowing the interferon-cell line mixtures to incubate for from 0 to 1 hour;

c. adding challenge virus preparation to each of the said segregated, serially diluted interferon-cell line mixtures and allowing the resulting mixtures to incubate for from about 12 to 16 hours;

d. providing a virus control mixture comprising said challenge virus preparation, and a cell control comprising said viable cell line preparation;

e. providing an interferon sample of known titer;

f. reading said assay mixtures when the said virus control mixture shows 100% cytopathic effect;

whereby the titer of interferon in said sample is determined as the reciprocal of the dilution of the mixture showing a 50% reduction in cytopathic effect as compared to the virus and cell controls.

DETAILED DESCRIPTION OF THE INVENTION

The entire assay can be carried out in from 12 to 16 hours from initiation of the procedure, thus making it practical for use in clinical applications and more efficient and desirable than previously available procedures for monitoring the preparation and purification of interferon. The subject assay can be used to detect interferon derived from any animal source, including, for example, human (whether leukocyte or fibroblast), feline, canine, rat, mouse, bovine, rabbit, chicken and hamster interferon.

In its clinical aspect, the disclosed assay is particularly applicable in situations where the only information being sought is relative increase in interferon titer rather than absolute titer. For example, in a blood sample, background impurities such as nonspecific viral inhibitors produce interferon-like activity. Hence, a baseline or residual titer will usually appear unless specifically removed by acid treatment, incubation at temperatures which destroy the impurities or some other cleanup method. That indeed the specific interferon is being measured rather than a non-specific antiviral agent can be ascertained in many ways, such as by supplementary assays on cells insensitive to the interferon in question (such as cells of another animal species) or by the use of antiserum to the interferon in question.

However, if relative increase is all that is being sought to monitor blood levels in patients treated with interferon, all that is necessary is to establish the baseline titer for a given individual and to measure this increase in titer from the baseline level of interferon.

An example of such a situation would be a carefully contracted clinical study in which blood samples are taken at $T_o$ and the interferon-like activity measured. Upon the injection of interferon, blood samples would be taken and interferon levels determined as a function of time. The increase in titer over the baseline would thus be measurable by the assay of this invention as indicated by the results of clinical data shown in Table 1.

The assay of the instant invention can also be applied in a situation where background titer for a given individual is unavailable. For example, the disclosed assay may be used as a screening test to determine whether or not an infection is of a viral nature. In such a situation, background titer would typically be unavailable, however, the relative increase in interferon level can be determined by comparing the increase to a baseline titer level for a sampling of healthy, normal human donors as indicated in Table II.

The assay of the instant invention can be performed on samples of whole blood, serum or plasma, with the proviso that when whole blood samples are used, the titer being measured must exceed 80 in order to be detected over blood cells present. Note Table III.

The assay of the present invention can utilize any conventional cell line known to be sensitive to the interferon type to be assayed. Suitable cell lines for this purpose include bovine kidney cells, which is a continuous epithelial cell line sensitive to human leukocyte interferon, GM258 or FS-7, human fibroblast cell lines sensitive to human leukocyte or fibroblast interferon, L929, mouse fibroblasts sensitive to mouse interferon, RK-13, rabbit epithelial cells sensitive to rabbit interferon, and other cell lines well known in the art.

The challenge virus employed may be one of several viruses. Examples of suitable challenge viruses include vesicular stomatitis virus (VSV), sindbis virus (Semliki forest virus) and other challenge viruses well known in the art.

The components of the improved assay method of the instant invention are conveniently packaged in a kit. A typical kit would contain, in several containers, the viable cell preparation, the challenge virus and a reference standard interferon. The kit might additionally contain a suitable dye for the disclosed bioassay.

The cell preparation would preferably be packaged in the form of a suspension (maintained at 4° C.) in order to allow for immediate commencement of the bioassay procedure upon performance of the serial twofold dilutions. In such a case, the preferred form of the cells might be a 1x or 10x suspension. Alternatively, the cells could be shipped as confluent monolayers.

The challenge virus can be packaged in any suitable container conforming to government regulations for a given grade etiological agent. For example, VSV can be packaged in a dual-walled container which has an impenetrable inner wall. The virus may be sent in a frozen state ($-20°$ C.) or in a lyophilized state.

The reference interferon may be shipped in the lyophilized state or at a decreased temperature state to insure preservation.

In a preferred embodiment of the invention, an assay for human leukocyte interferon is described. This preferred embodiment utilizes bovine kidney cells (MDBK) as the cell culture and vesicular stomatitis virus as the challenge virus.

DESCRIPTION OF THE PREFERRED EMBODIMENTS

Minimal Essential Medium with Earl's salts is supplemented with 10% (v/v) heat-inactivated fetal calf serum (FCS) and an antibiotic such as penicillin, streptomycin or gentamicin (Medium I). Stock cultures of bovine kidney cells are grown and maintained in flasks (75cm$^2$) in Medium I at 37° C. The cultures were routinely passaged every 3-4 days by trypsinization of the monolayers with a 1:3 dispersion of the cells. For the assay, the cells are trypsinized from the stock flask and diluted in Medium I to form a suspension having a concentration of $4 \times 10^5$ cells/ml.

A supply of virus (VSV) is prepared by infecting mouse L cells. Supernatent fluids are harvested, dispensed in 1.0 ml aliquots and stored at $-70°$ C. The titer of the pool is determined by the plaque assay procedure. One such pool had a titer of $7.6 \times 10^7$ plaque-forming units (PFU)/ml. For the assay, the stock virus was diluted in Medium I to $4 \times 10^4$ PFU/0.05 ml.

Reference human leukocyte interferon (NIH #G-023-901-527) was obtained in the lyophilized state and reconstituted in 1.0 ml of sterile distilled water. A stock leukocyte standard of approximately 625 units/ml for the assay was prepared by diluting the reference interferon 1:32 in Medium I.

PROCEDURE

1. Dispense 0.1 ml of Medium I in 12 consecutive wells of a 96 well flat-bottomed microtiter plate.
2. Add 0.1 ml of the diluted reference interferon to well #1.
3. Serially transfer 0.1 ml from well #1 to well #2 and so on through well #12 (serial twofold dilutions).
4. Add 0.1 ml of the diluted cell suspension to each well. Note: This step increases the value of the dilution of each well twofold.
5. Seal plate with plastic sealer and incubate for 1 hour. Note: This incubation period is not critical and can be omitted.
6. Remove sealer and add 0.05 ml diluted VSV to each well. Note: Control wells are prepared as follows:

a. Virus control=cells+VSV No interferon
b. Cell control=cells No VSV or interferon
7. Seal plate and incubate 12-18 hours at 37° C.
8. Aspirate medium from all wells and discard.
9. Add 0.05 ml of a solution containing 0.5g of crystal violet in 100 ml of 70% aqueous methanol to each well for 1 minute. This step stains and fixes the cells to the well and inactivates any residual virus present.
10. Decant stain, rinse plate twice with tap water and air dry.
11. Read plate. The 50% end point, that is the well in which half the cells have been protected from VSV challenge, can be read microscopically in a stained or unstained plate or may also be determined by gross examination of an inverted stained plate with the aid of a white background or light table.

The assay is read when the virus control wells show a 100% cytopathic effect, i.e., total cell destruction by the virus. The titer of interferon is represented in the well showing a 50% reduction in CPE, as compared to the virus and cell control wells and is expressed (in units/ml) as the reciprocal of the dilution of that well.

EXAMPLE 1

A reference solution of interferon diluted 1:100 in distilled water and serially diluted twofold in the above assay gave a 50% CPE reduction when compared to the virus control well in well #5 (or the 1:64 dilution well). Therefore, by definition, that well contains 1 unit of interferon/ml, and the original solution contains 6400 units/ml.

It should be further noted that any conventional dye system can be employed to assist in the reading step. Other suitable stains include methylrosaniline chloride, trypan blue, giemsa, and neutral red.

It is evident that, in comparison to prior art procedures for assaying for interferon, the above procedure offers the substantial advantages of rapidity and simplicity. The entire assay can be run and read on an "overnight basis" i.e., in about 18 hours or even less. This result is based essentially on the unexpected discovery that the two main incubation periods believed to be critical in the prior art procedures can be severely shortened and that one may be eliminated altogether. Thus, for example, the overnight incubation of interferon samples with a cell monolayer has been eliminated and replaced with an incubation period of from 0 to 1 hour (Step 5) with a cell suspension. Additionally, rather than decanting off the interferon solution after incubation, the present method provides for addition of the challenge virus directly to the interferon containing medium (Step 6). The 24-hour or more incubation of the challenge virus with the cell medium has also been substantially reduced to a total of 12 to 18 hours (Step 7).

EXAMPLE 2

Table 1 shows interferon-like activity in the sera of cancer patients receiving intramuscular injections of human leukocyte interferon. Samples of blood sera were taken prior to injection of $3 \times 10^6 - 6 \times 10^6$ units of interferon (indicated by pre=20 on 2/10/78, pre=40 on 2/27/78, pre=20 on 3/14/78 and pre=80 on 3/15/78). Thus, the background titer was established for the individuals who were to be injected. Samples of blood sera were taken at the times noted. As can be seen, there was a sharp increase in titer in each case, an increase which is attributable to higher interferon levels.

As a control, to assure that the increase in titer was actually attributable to interferon activity, the assay was run using rabbit kidney cells (RK-13) which are relatively insensitive to human interferon. As can be seen in each case, the titer figures remained low, which would be expected with a cell line which is relatively insensitive to human interferon activity. It is thus clear that the increase in titer measured in MDBK cells is most likely attributable to interferon and not to non-specific inhibitors.

TABLE 1

Interferon-Like Activity in the Sera of Cancer Patients Receiving Human Leukocyte Interferon

| Test Specimen | Date | Time[b] | Interferon-Titer[a] Cell Line MDBK[c] | Rabbit Kidney-13[d] |
|---|---|---|---|---|
| Patient 1 | 8/10/78 | 0 hr | 10 | <10 |
| | 8/10/78 | 6 hr | 80 | <10 |
| | 8/11/78 | 24 hr | 20 | <10 |
| | 8/17/78 | 0 hr | 40 | <10 |
| | 8/17/78 | 6 hr | 80 | <10 |
| | 8/18/78 | 24 hr | 20 | <10 |
| Patient 2 | 9/08/78 | 0 hr | 40 | <10 |
| | 9/08/78 | 3 hr | 80 | <10 |
| | 9/09/78 | 24 hr | 80 | <10 |
| Patient 3 | 7/27/78 | 0 hr | 10 | 10 |
| | 7/27/78 | 6 hr | 80 | 10 |
| | 7/28/78 | 24 hr | 20 | 10 |
| | 8/03/78 | 0 hr | 20 | <10 |
| | 8/03/78 | 6 hr | 80 | <10 |
| | 8/04/78 | 24 hr | 40 | <10 |
| Patient 4 | 3/14/78 | 0 hr | 20 | <10 |
| | 3/14/78 | 3 hr | 160 | <10 |
| | 3/14/78 | 6 hr | 160 | <10 |
| | 3/14/78 | 12 hr | 160 | <10 |
| Patient 5 | 3/06/78 | 0 hr | 20 | <10 |
| | 3/06/78 | 3 hr | 80 | <10 |
| | 3/06/78 | 6 hr | 160 | <10 |
| | 3/06/78 | 12 hr | 80 | <10 |
| | 3/07/78 | 24 hr | 40 | <10 |

[a]Reciprocal of specimen dilution at which microscopic examination indicated that ≧50% of cells were protected against cytopathogenic effect (CPE) induced by vesicular stomatitis virus.
[b]In relation to intramuscular injection of human leukocyte interferon at 0 hr.
[c]Continuous line of steer kidney cells sensitive to human leukocyte interferon.
[d]Continuous line of rabbit kidney cells relatively insensitive to human leukocyte interferon.

EXAMPLE 3

Table 2 shows the interferon-like activity of sera from normal human donors in the absence of interferon injection. Such a sampling can be used to establish a background standard in situations where an individual's background would typically be unavailable, such as in a case where it is desired to determine if an infection is of a viral nature.

EXAMPLE 4

A test solution of human fibroblast interferon was diluted 1:40 in well #1 of the assay set up and run as previously described with GM 258 as the test cell. A 50% end point was determined at well #8 (1:5120) as previously described. Therefore, the titer of the fibroblast interferon is read as 5120 units/ml.

The fact that such basic modifications to the prior art procedures could be made without adversely affecting the accuracy or sensitivity of the assay must be considered most unexpected.

TABLE II

Interferon-Like Activity of Sera from Normal Human Donors

| Donor # | Intereferon Titer |
| --- | --- |
| 1 | 10 |
| 2 | 10 |
| 3 | <10 |
| 4 | -10 |
| 5 | 10 |
| 6 | 20 |
| 7 | 10 |
| 8 | 10 |
| 9 | 10 |
| 10 | 10 |
| 11 | 10 |
| 12 | 20 |
| 13 | 10 |
| 14 | 10 |
| 15 | 20 |
| 16 | 20 |
| 17 | 20 |
| 18 | 10 |
| 19 | 10 |
| 20 | 10 | a. Reciprocal of dilution at which ≧50% of MDBK cells examined microscopically did not exhibit virus CPE.

TABLE III

Stability of Human Leukocyte Interferon in Human Serum, Plasma, Whole Blood, Fetal Calf Serum or Tissue Culture Medium[a]

| Specimen Tested | Interferon Titer |
| --- | --- |
| Human serum #23 | 10 |
| Human plasma #23 | 10 |
| Human whole blood #23[b] | — |
| Fetal calf serum (FCS)[c] | <10 |
| Human leukocyte interferon 50A diluted 1-10 in MEM + 10% FCS | 400 |
| Human leukocyte interferon 50A diluted 1-10 in human serum #23 | 800 |
| Human leukocyte interferon 50A diluted 1-10 in human plasma #23 | 1600 |
| Human leukocyte interferon 50A diluted 1-10 in human whole blood #23 | 800 |
| Human leukocyte interferon 50A diluted 1-10 in fetal calf serum | 400 |

[a] Human leukocyte interferon 50A was initially diluted 1-10 in tissue culture medium (MEM), human serum, human plasma, human whole blood or fetal calf serum (FCS). After 1 hr. incubation at room temperature, test specimens were further diluted using MEM containing 10% FCS and tested for their ability to protect MDBK against challenge with VSV (MOI-10).
[b] Presence of human blood cells prevented microscopic observation of MDBK monolayers at dilutions of whole blood corresponding to dilutions of 1-10 through 1-80. At a dilution of 1-160, >95% monolayer exhibited virus CPE.
[c] Heat-inactivated at 56° C. for 60 min.

We claim:

1. An improved assay for interferon comprising the following steps in combination:
   a. contacting a serially diluted and segregated interferon containing sample in the presence of a cell support medium with a viable cell line preparation in the form of a cell suspension, said cell line known to be sensitive to the interferon type to be assayed, so as to form an interferon-cell line mixture in the form of a suspension;
   b. allowing said interferon-cell line mixture to incubate from 0 to 1 hour;
   c. adding a challenge virus preparation to each of said segregated, serially diluted interferon-cell line mixtures and allowing the resulting mixtures to incubate from about 12 to 18 hours;
   d. providing a virus control mixture comprising said viable cell line preparation and said challenge virus preparation, and a cell control comprising said viable cell line preparation;
   e. reading said assay mixtures when the said virus control mixture shows 100% cytopathic effect, whereby the titer of interferon in said sample is determined as the reciprocal of the dilution of the mixture showing a 50% reduction in cytopathic effect as compared to the virus and cell controls.

2. The assay of claim 1 wherein said interferon containing sample consists of human leukocyte or human fibroblast interferon.

3. The assay of claim 2 wherein said cell line consists of bovine kidney cells and said challenge virus is vesicular stomatitis virus.

4. The assay of claim 3 wherein said assay is read after staining of the cell preparations.

5. The assay of claim 4 wherein the dye-fixative solution is crystal violet in methanol.

6. The assay of claim 1 wherein the said incubation steps are carried out at a temperature of about 37° C.

* * * * *